US00PP16188P2

(12) United States Plant Patent
Taylor

(10) Patent No.: US PP16,188 P2
(45) Date of Patent: Jan. 3, 2006

(54) ***PITTOSPORUM* PLANT NAMED 'CNI THREE'**

(50) Latin Name: *Pittosporum tobira*
Varietal Denomination: CNI Three

(75) Inventor: Keith Taylor, Lumberton, NC (US)

(73) Assignee: Carolina Nurseries, Inc., Moncks Corner, SC (US)

( * ) Notice: Subject to any disclaimer, the term of this patent is extended or adjusted under 35 U.S.C. 154(b) by 16 days.

(21) Appl. No.: 11/041,617

(22) Filed: Jan. 22, 2005

(51) Int. Cl.
*A01H 5/00* (2006.01)

(52) U.S. Cl. ..... Plt./234

(58) Field of Classification Search ..... Plt./234
See application file for complete search history.

*Primary Examiner*—Bruce R. Campell
*Assistant Examiner*—S. B. McCormick-Ewoldt
(74) *Attorney, Agent, or Firm*—C. A. Whealy

(57) ABSTRACT

A new and distinct *Pittosporum* plant named 'CNI Three', characterized by its compact and roughly hemispherical plant form; freely branching habit; dense and bushy plant habit; relatively small green and pale yellow variegated leaves; tolerant to full sun and partial shade conditions; and tolerant to low temperatures.

2 Drawing Sheets

Botanical designation: *Pittosporum tobira.*
Cultivar denomination: 'CNI Three'.

BACKGROUND OF THE INVENTION

The present invention relates to a new and distinct cultivar of *Pittosporum,* botanically known as *Pittosporum tobira,* and hereinafter referred to by the name 'CNI Three'.

The new *Pittosporum* is a naturally-occurring branch mutation of *Pittosporum tobira* cultivar Wheeler's Dwarf, not patented. The new *Pittosporum* was discovered and selected by the Inventor in a controlled environment in Lumberton, N.C. in October, 1994 within a population of plants of the cultivar Wheeler's Dwarf. The selection of this branch mutation was based on its variegated leaves.

Asexual reproduction of the new *Pittosporum* by cuttings in a controlled environment in Lumberton, N.C., since the spring of 1998, has shown that the unique features of this new *Pittosporum* are stable and reproduced true to type in successive generations.

SUMMARY OF THE INVENTION

The cultivar CNI Three has not been observed under all possible environment conditions. The phenotype may vary somewhat with variations in environment and cultural practices such as temperature and light intensity without, however, any variance in genotype.

The following traits have been repeatedly observed and are determined to be the unique characteristic of 'CNI Three'. These characteristics in combination distinguish 'CNI Three' as a new and distinct cultivar of *Pittosporum :*

1. Compact and roughly hemispherical plant form.
2. Freely branching habit; dense and bushy plant habit.
3. Relatively small green and pale yellow variegated leaves.
4. Tolerant to full sun and partial shade conditions.
5. Tolerant to low temperatures.

Plants of the new *Pittosporum* differ from plants of the parent, the cultivar Wheeler's Dwarf, in the following characteristics:

1. Plants of the new *Pittosporum* are more compact than plants of the cultivar Wheeler's Dwarf.
2. Plants of the new *Pittosporum* have smaller leaves than plants of the cultivar Wheeler's Dwarf.
3. Plants of the new *Pittosporum* and the cultivar Wheeler's Dwarf differ in leaf coloration as plants of the cultivar Wheeler'Dwarf have solid green-colored leaves.

Plants of the new *Pittosporum* can be compared to plants of the *Pittosporum* cultivar Lauralee, disclosed in U.S. Plant Pat. No. 5,893. In side-by-side comparisons conducted in Moncks Corner, S.C., plants of the new *Pittosporum* differed from plants of the cultivar Lauralee in the following characteristics:

1. Plants of the new *Pittosporum* were more compact than plants of the cultivar Lauralee.
2. Plants of the new *Pittosporum* had smaller leaves than plants of the cultivar Lauralee.
3. Plants of the new *Pittosporum* and the cultivar Lauralee differed in leaf variegation pattern.

Plants of the new *Pittosporum* can be compared to plants of the *Pittosporum* cultivar Turner's Variegated Dwarf, disclosed in U.S. Plant Pat. No. 4,919. In side-by-side comparisons conducted in Moncks Corner, S.C., plants of the new *Pittosporum* differed from plants of the cultivar Turner's Variegated Dwarf in the following characteristics:

1. Plants of the new *Pittosporum* were more compact than plants of the cultivar Turner's Variegated Dwarf.
2. Plants of the new *Pittosporum* had smaller leaves than plants of the cultivar Turner's Variegated Dwarf.
3. Plants of the new *Pittosporum* were more cold hardy than plants of the cultivar Turner's Variegated Dwarf.
4. Plants of the new *Pittosporum* were not susceptible to Leaf Spot whereas plants of the cultivar Turner's Variegated Dwarf were susceptible to Leaf Spot.

BRIEF DESCRIPTION OF THE PHOTOGRAPHS

The accompanying colored photographs illustrate the overall appearance of the new *Pittosporum*, showing the colors as true as it is reasonably possible to obtain in colored reproductions of this type. Colors in the photographs may differ slightly from the color values cited in the detailed botanical description which accurately describe the colors of the new *Pittosporum* .

The photograph on the first sheet is a close-up view of typical leaves of 'CNI Three'.

The photograph on the second sheet comprises a side perspective view of typical plants of 'CNI Three' grown in an outdoor nursery.

DETAILED BOTANICAL DESCRIPTION

The aforementioned photographs and following observations and measurements describe plants grown in Moncks Corner, S.C., grown in five-gallon containers in an outdoor nursery during the spring and summer and under conditions which closely approximate commercial production. During the production of the plants, day temperatures ranged from 21 to 32° C. and night temperatures ranged from 12 to 26° C. Plants were about two years old when the photographs and the description were taken. Plants were pruned to maintain the plant's symmetry. In the description color references are made to The Royal Horticultural Society Colour Chart, 1995 Edition, except where general terms of ordinary dictionary significance are used.

Botanical classification: *Pittosporum tobira* cultivar CNI Three.

Parentage: Naturally-occuring branch mutation of *Pittosporum tobira* cultivar Wheeler's Dwarf, not patented.

Propagation:

*Type.*—By cuttings.

*Time to initiate roots, summer.*—About 20 days at 29° C.

*Time to initiate roots, winter.*—About 41 days at 18° C.

*Time to produce a rooted young plant, summer.*—About four months at 29° C.

*Time to produce a rooted young plant, winter.*—About six months at 18° C.

*Root description.*—Fine; light brown in color.

*Rooting habit.*—Freely branching; moderately dense.

Plant description:

*Plant type.*—Perennial evergreen subshrub.

*Plant form and growth habit.*—Compact and roughly hemispherical plant form. Upright and outwardly spreading growth habit. Low to moderate vigor.

*Branching habit.*—Freely branching; dense and bushy plant habit; usually about four main branches each with about six lateral branches.

*Plant height.*—About 27 cm.

*Plant diameter* (*area of spread*).—About 55 cm.

*Lateral branch description.*—Length, primary branches: About 12 cm. Length, lateral branches: About 11 cm. Diameter, primary branches: About 1.1 cm. Diameter, lateral branches: About 5 mm. Internode lenghth: About 7 mm. Aspect: Upright and outwardly spreading. Texture, immature: Pubescent. Texture, mature: Woody, rough. Color, immature: Close to 145A with brownish tinge. Color mature: Closest to 199A.

*Foliage description.*—Arrangement: Whorled, simple. Length: About 5.75 cm. Width: About 2.6 cm. Shape: Oblanceolate. Apex: Acute to obtuse. Base: Cuneate. Margin: Entire. Texture, upper and lower surfaces: Smooth, glabrous; leathery. Venation pattern: Pinnate. Color: Developing leaves, upper surface: Centers, between 144A and 146A; towards the margins, 151A to 151C. Developing leaves, lower surface: Centers, between 146B and 146D; towards the margins, close to 160A. Fully expanded leaves, upper surface: Centers, more green than 191A; towards the margins, 160C to 158A. Fully expanded leaves, lower surface: Centers, more green than 191A; towards the margins, 160D to 158A. Venation, upper and lower surfaces: Close to 145C. Petiole: Length: About 8 mm. Diameter: About 2 mm. Texture, upper and lower surfaces: Smooth, glabrous; leathery. Color, upper and lower surfaces: Close to 145C.

Flower description: Flower development has not been observed on plants of the new *Pittosporum*.

Disease/pest resistance: Plants of the new *Pittosporum* have been observed to be relatively resistant to root rot pathogens, such as *Phytophthora*. Plants of the new *Pittosporum* have not been observed to be resistant to other pathogens and pests common to *Pittosporum*.

Garden performance: Plants of the new *Pittosporum* have been observed to have excellent tolerance to wind, rain and temperatures from −13° C. to 39° C.

It is claimed:

1. A new and distinct *Pittosporum* plant named 'CNI Three', as illustrated and described.

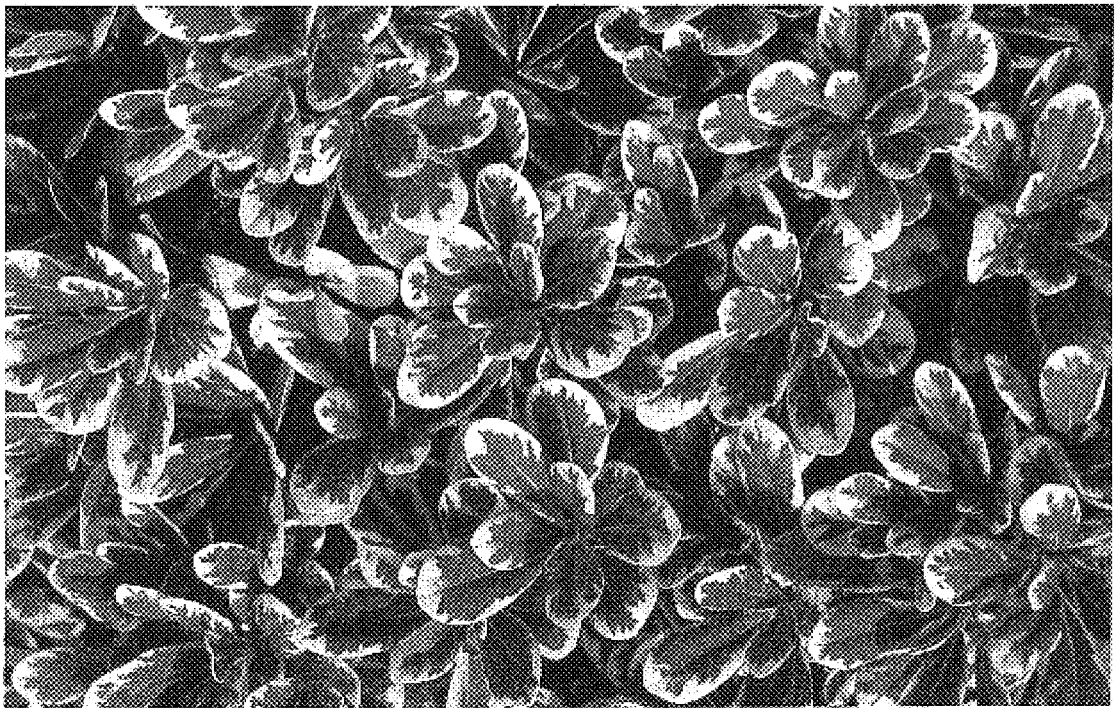

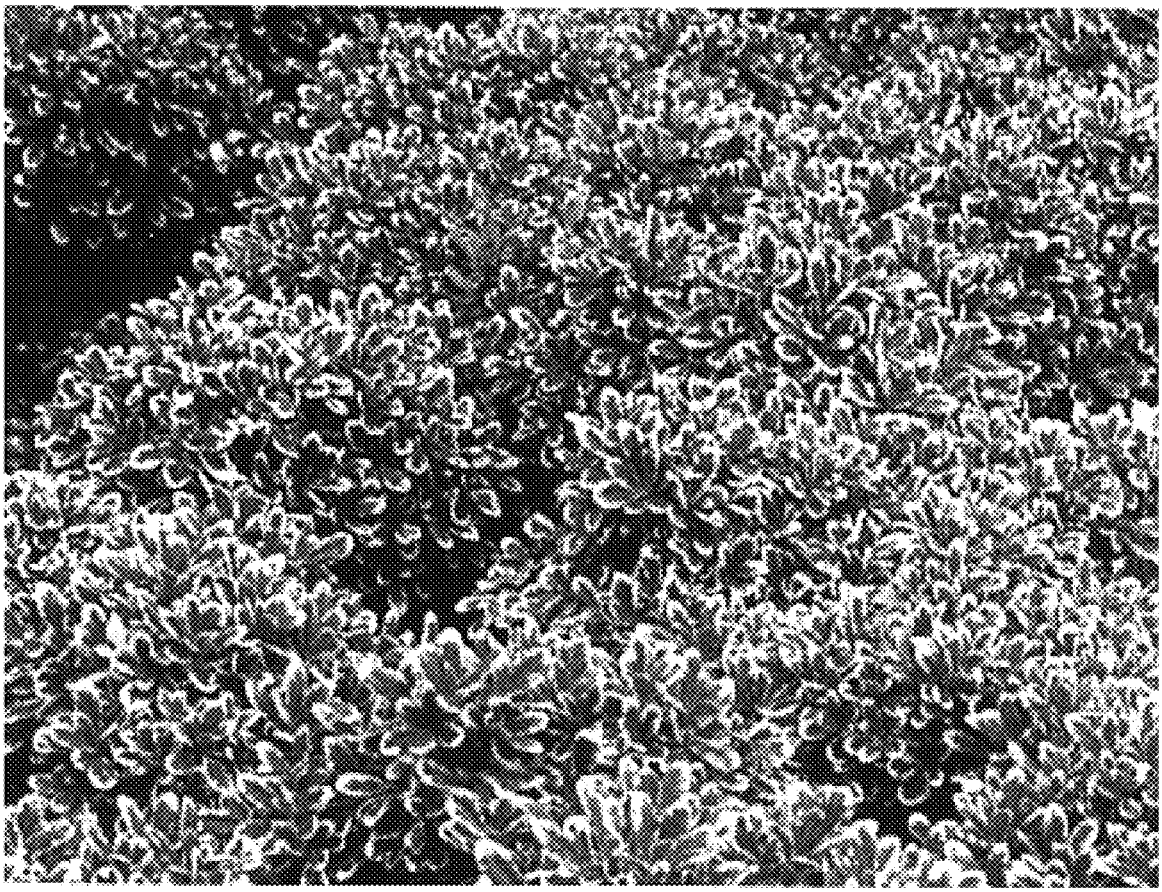

* * * * *